US012575952B2

(12) United States Patent
Nakayama et al.

(10) Patent No.: US 12,575,952 B2
(45) Date of Patent: Mar. 17, 2026

(54) INTRAVASCULAR INDWELLING STENT

(71) Applicant: BIOTUBE CO., LTD, Tokyo (JP)

(72) Inventors: Yasuhide Nakayama, Tokyo (JP);
Hisashi Sugiura, Shinshiro (JP);
Takaharu Tanaka, Nagoya (JP)

(73) Assignee: BIOTUBE CO., LTD, Chuo-ku (JP)

( * ) Notice: Subject to any disclaimer, the term of this patent is extended or adjusted under 35 U.S.C. 154(b) by 589 days.

(21) Appl. No.: 18/016,042

(22) PCT Filed: Jul. 15, 2021

(86) PCT No.: PCT/JP2021/026608
§ 371 (c)(1),
(2) Date: Jan. 13, 2023

(87) PCT Pub. No.: WO2022/014673
PCT Pub. Date: Jan. 20, 2022

(65) Prior Publication Data
US 2023/0270574 A1     Aug. 31, 2023

(30) Foreign Application Priority Data
Jul. 17, 2020     (JP) ................................. 2020-123048

(51) Int. Cl.
*A61F 2/90*          (2013.01)
*A61B 17/12*         (2006.01)
(Continued)

(52) U.S. Cl.
CPC .......... *A61F 2/90* (2013.01); *A61B 17/12168* (2013.01); *A61F 2002/0081* (2013.01);
(Continued)

(58) Field of Classification Search
CPC ... A61F 2/07; A61F 2250/0023; A61L 31/146
See application file for complete search history.

(56) References Cited

U.S. PATENT DOCUMENTS 4,739,762 A * 4/1988 Palmaz ................... A61F 2/915
623/1.46
2006/0036311 A1 2/2006 Nakayama
(Continued)

FOREIGN PATENT DOCUMENTS

EP          1923025 A2     5/2008
JP      2004261567 A       9/2004
(Continued)

OTHER PUBLICATIONS

Translation of JP 2005312584 (Year: 2005).*
(Continued)

*Primary Examiner* — Brian E Pellegrino
(74) *Attorney, Agent, or Firm* — Bochner PLLC; Andrew D. Bochner

(57) ABSTRACT

Disclosed is an intravascular indwelling stent that include a stent main body and a polymer film covering the stent main body. Through-holes are formed in the polymer film. The through-holes connect an inside and an outside of a cylinder of the intravascular indwelling stent to each other and each have an opening size of 0.02 mm or more and 0.2 mm or less. An opening occupancy, which is the ratio of the opening area of all the through-holes included in a unit area of the outer surface of the polymer film to the unit area, is 25% or more and 41% or less. A surface density of boundary, which is the ratio of the length of opening edges of all the through-holes included in a unit area of the outer surface of the polymer film to the unit area, is 9.5/mm or more and 30/mm or less.

5 Claims, 7 Drawing Sheets

(51) Int. Cl.
*A61F 2/00*        (2006.01)
*A61F 2/07*        (2013.01)

(52) U.S. Cl.
CPC ......... *A61F 2/07* (2013.01); *A61F 2210/0076*
      (2013.01); *A61F 2230/0069* (2013.01); *A61F*
      *2250/001* (2013.01)

(56)                    References Cited

U.S. PATENT DOCUMENTS

| | | |
|---|---|---|
| 2007/0255388 A1 | 11/2007 | Rudakov et al. |
| 2008/0167708 A1 | 7/2008 | Molland et al. |
| 2009/0054966 A1* | 2/2009 | Rudakov ............ C08G 18/2885 623/1.15 |
| 2017/0128244 A1 | 5/2017 | Nakayama et al. |

FOREIGN PATENT DOCUMENTS

| | | | |
|---|---|---|---|
| JP | 2004313322 A | | 11/2004 |
| JP | 2005312584 A | * | 11/2005 |
| JP | 2012055649 A | | 3/2012 |

OTHER PUBLICATIONS

International Search Report of the International Searching Authority dated Aug. 10, 2021, in related International Appl. No. PCT/JP2021/026608, 5 pages.
Extended European search report of the European Patent Office in related European Patent Appl. No. 21843535.2, dated Jul. 3, 2024, 8 pages.

* cited by examiner

INTRAVASCULAR INDWELLING STENT

TECHNICAL FIELD

The present invention relates to an intravascular indwelling stent that is indwelled in a blood vessel.

BACKGROUND ART

Studies have been conducted on use of an intravascular indwelling stent as a method for surgical treatment of an aneurysm caused by local weakening of a blood vessel wall. In vascular surgery for embolizing an aneurysm opening portion with an intravascular indwelling stent indwelled at an aneurysm generation site, inflow of blood into an aneurysm is blocked by the intravascular indwelling stent to clot the blood in the aneurysm. Treatment using an intravascular indwelling stent does not involve a massive incision through laparotomy or craniotomy, unlike treatment in which a blood vessel having an aneurysm is replaced by an artificial blood vessel, or treatment in which a neck of an aneurysm is clamped with a clip.

Vascular endothelial cells that release vasoactive substances to adjust vascular tone and blood coagulation form the vascular endothelium in the blood vessel where an intravascular indwelling stent is indwelled. Many antithrombogenic substances, such as thrombomodulin, heparin-like substances, prostacyclin, nitric oxide, and tissue plasminogen actin beta, are produced in the vascular endothelium. An intravascular indwelling stent in which the entire surface of a strut is covered with a polymer film also suppresses blood clot formation caused by a metallic strut with the inner circumferential surface of the intravascular indwelling stent as a smooth surface.

The intravascular indwelling stent covered with a polymer film also suppresses thickening of the intima derived from platelets in the blood clot. Very small through-holes formed in the polymer film promote entry of vascular endothelial cells to the inside of the intravascular indwelling stent. Promotion of entry of vascular endothelial cells accelerates intimal formation from the intravascular indwelling stent, and further suppresses thickening of the neointima. As an example, through-holes formed in the polymer film have a diameter of, for example, 100 μm, and are linearly arranged at intervals of 200 μm. The rows of linearly arranged through-holes are arranged at equal intervals in a direction along a circumferential direction of the stent having a diameter of 8 mm with the central angle being 15° (see, for example, Patent Documents 1 and 2).

There are not a few cases where a branch blood vessel extends from a body part of an aneurysm as in an aneurysm generated at a branch portion between the internal carotid artery and the posterior communicating artery. The intravascular indwelling stent with through-holes formed in the polymer film closes the branch opening of the branch blood vessel while suppressing thickening of the neointima to embolize the aneurysm opening portion in the aneurysm. The intravascular indwelling stent described in Patent Document 3 has a configuration in which the opening occupancy by very small through-holes is 20% or more and 50% or less for the purpose of embolizing the aneurysm opening portion in the aneurysm and ensuring blood flow in the branch blood vessel (see, for example, Patent Document 3).

CITATIONS LIST

Patent Literature

Patent Document 1: Japanese Laid-Open Patent Publication No. 2004-261567

Patent Document 2: Japanese Laid-Open Patent Publication No. 2004-313322
Patent Document 3: Japanese Laid-Open Patent Publication No. 2012-55649

SUMMARY OF INVENTION

Technical Problems

Meanwhile, the range of the opening occupancy disclosed in Patent Document 3 is determined on the basis of fluid analysis using a blood vessel model. For example, when the opening occupancy of very small through-holes is high, the blood flowing into an aneurysm from the downstream of an aneurysm opening portion makes one rotation in the upstream direction along the inner wall of the aneurysm and flows out from the upstream of the aneurysm opening portion. In contrast, when the opening occupancy of very small through-holes is low, the blood flowing into an aneurysm from the upstream of an aneurysm opening portion makes one rotation in the downstream direction along the inner wall of the aneurysm and flows out from the downstream of the aneurysm opening portion. On the basis of the analysis results showing that the flow pattern in the aneurysm is reversed, an opening occupancy of 25% or more and 50% or less is determined as a range in which the flow of blood in the aneurysm substantially stops.

On the other hand, an arterial treating stent indwelled in a blood vessel is recognized as a foreign substance by biological tissue materials such as vascular endothelial cells. The intravascular indwelling stent recognized as a foreign substance is covered with a connective tissue produced by vascular endothelial cells or the like and is thereby formed into an intima so as not to be recognized as a foreign substance in the blood vessel. In the analysis of working fluid using a blood vessel model, intimal formation is not considered, and of course, a factor of intimal formation at an aneurysm opening portion (i) and a factor of intimal formation at a branch opening (ii) are not considered. Consequently, in the use of the intravascular indwelling stent for surgical treatment of an aneurysm or the like, there is still room for improvement from the viewpoint of maintaining the inflow of blood into the branch blood vessel and ensuring that blood hardly flows in the aneurysm.

Moreover, as described above for the intimal formation, entry of a biological tissue material contributing to intimal formation to the inside of the intravascular indwelling stent is promoted as the opening of the through-hole becomes larger, and the factor of intimal formation includes not only ease of passage of the biological tissue material (iii) through the opening of the through-hole but also ease of exhibiting a self-defense function (iv) by the biological tissue material. In the determination of the opening occupancy of through-holes per unit area, as a main factor of intimal formation, ease of passage of the biological tissue material (iii) is considered, but ease of exhibiting a self-defense function (iv) is hardly reflected.

An object of the present invention is to provide an intravascular indwelling stent which achieves both a blood flow conservation property of a branch blood vessel and an aneurysm opening portion embolization property.

Solutions to Problems

An intravascular indwelling stent for solving the above-described problems is an intravascular indwelling stent indwelled in a blood vessel. The intravascular indwelling stent includes a stent main body being diametrically expandable and having a tubular shape, and a polymer film covering the stent main body. The polymer film includes through-holes connecting the inside and the outside of a cylinder of the intravascular indwelling stent to each other and each having an opening size of 0.02 mm or more and 0.2 mm or less. The ratio of the opening area of all the through-holes included in a unit area of the outer surface of the polymer film to the unit area is an opening occupancy. The ratio of the length of opening edges of all the through-holes included in a unit area of the outer surface of the polymer film to the unit area is a surface density of boundary. The opening occupancy is 25% or more and 41% or less, and the surface density of boundary is 9.5/mm or more and 30/mm or less.

In the course of extensively conducting studies on a process in which the intravascular indwelling stent is covered with a biological tissue material, the inventors of the present application have found that formation of a connective tissue covering the intravascular indwelling stent starts to occur with opening edges of through-holes as formation initiation points. That is, the inventors have found that a foreign substance recognition reaction and an encapsulation reaction resulting from contact of the biological tissue material with an artificial material proceed with opening edges of through-holes as formation initiation points. In other words, the inventors have found that production of collagen is started with opening edges of through-holes as formation initiation points, so that the connective tissue spreads from the opening edges of the through-holes to the entire surface of the polymer film. The inventors have found that the connective tissue, beginning to be formed with the opening edges of the through-holes as the formation initiation points, grows to cover the surface of the polymer film that separates the through-holes from each other, whereby the polymer film is formed into an intima to form a neointima.

(A) In the process of the intimal formation described above, the length of the opening edges defining the through-holes and, moreover, the surface density of boundary obtained by normalizing the length of the opening edges defining the through-holes per unit area indicate the size of a site where intimal formation starts within the unit area, i.e. the size of a formation initiation point. In other words, the surface density of boundary serves as an indication of ease of exhibiting a self-defense function (iv) by the biological tissue material, and as indications of ease of progress of intimal formation in an aneurysm opening portion (i) and ease of progress of intimal formation in a branch opening (ii).

(B) In the process of the intimal formation described above, the area occupied by the openings of the through-holes and, moreover, the opening occupancy obtained by normalizing the opening area of the through-holes per unit area are an indication of the magnitude of an area that should be covered by the connective tissue not later than completion of intimal formation with the polymer film. In other words, the opening occupancy serves as an indication of the magnitude of the surface area of the polymer film to be formed into an intima, and as an indication of ease of passage of the biological tissue material (iii) through the openings of the through-holes.

(C) Of the polymer film forming the outer surface of the intravascular indwelling stent, a portion that is in direct contact with the vascular intima and a portion located at the aneurysm opening portion where the blood flow stagnates in the vicinity of the vascular intima are portions where cells and the like contained in the biological tissue material move easily, and in this portion of the polymer film, intimal formation proceeds relatively easily. On the other hand, a portion of the polymer film, which is located at the branch opening through which blood continues to flow, is a portion to which cells contained in the biological tissue material are less likely to be attached, and in this portion of the polymer film, intimal formation relatively hardly proceeds.

For ensuring both patency of the branch blood vessel and intimal formation there, increasing the opening occupancy to facilitate flow of blood is effective, but this approach alone is insufficient, and it is necessary that intimal formation from the polymer film proceed even in an environment where the blood continues to flow. That is, it is necessary to determine the surface density of boundary from the above-described technical viewpoints (A) to (C) so that production of collagen proceeds even in an environment where cells contained in the biological tissue material are less likely to be attached to the surface of the artificial material. In this respect, the intravascular indwelling stent facilitates achievement of patency of the branch blood vessel and intimal formation there because the opening occupancy is 25% or more and the surface density of boundary is 9.5/mm or more.

For ensuring both embolization of the aneurysm and intimal formation there, reducing the opening occupancy to resist flow of blood is effective, but this approach is radical for additionally achieving patency of the branch blood vessel, and it is preferable that embolization of the aneurysm be achieved after intimal formation from the polymer film. That is, it is necessary to determine the surface density of boundary from the above-described technical viewpoints (A) to (C) so that the through-holes are embolized after intimal formation in an environment where cells contained in the biological tissue material move easily to the surface of the artificial material. In this respect, the intravascular indwelling stent facilitates preservation of blood flow in the branch blood vessel while achieving embolization of the aneurysm opening portion because the opening occupancy is 41% or less and the surface density of boundary is 9.5/mm or more and 30/mm or less.

Thus, the intravascular indwelling stent improves the blood flow conservation property of the branch blood vessel and the aneurysm opening portion embolization property because the opening size is 0.02 mm or more and 0.2 mm or less, the opening occupancy is 25% or more and 41% or less, and the surface density of boundary is 9.5/mm or more and 30/mm or less.

In the intravascular indwelling stent, the through-holes may include through-holes having different opening sizes.

The intravascular indwelling stent is required to have strength sufficient to support a blood vessel wall, and have flexibility sufficient to follow bending of the blood vessel. Further, the intravascular indwelling stent is also required to have stress such that the blood vessel wall is pressed outward with a uniform pressure. Thus, setting the opening occupancy and the surface density of boundary within a specific range in the intravascular indwelling stent required to have various mechanical properties considerably restricts structural freedom in the intravascular indwelling stent. On the other hand, in a configuration in which the through-holes include through-holes having different opening sizes as in the above-described intravascular indwelling stent, it is possible to set a small opening size at a site required to have strength sufficient to support a blood vessel and set a large opening size at a site required to have flexibility. Further, since the opening size of each through-hole in the diametrically contracted intravascular indwelling stent is allowed to change to various sizes after diameter expansion, it is also possible to increase the degree of freedom of design in the intravascular indwelling stent in this respect.

In the intravascular indwelling stent, the polymer film may have a thickness of 1 μm or more and 100 μm or less.

The intravascular indwelling stent also improves the viability of the above-described effect of improving the blood flow conservation property of the branch blood vessel and the aneurysm opening portion embolization property because the thickness of the polymer film is determined, and thus the surface area of the polymer film to be formed into an intima is further specifically determined. In addition, when the thickness of the polymer film is 1 μm or more, breakage of the polymer film in the process of forming the polymer film is prevented to reduce labor required for forming the polymer film. When the thickness of the polymer film is 100 μm or less, an increase in depth of the through-hole, i.e. distance over which cells contained in the biological tissue material move, is suppressed so that the connective tissue required for intimal formation from the intravascular indwelling stent is easily formed inside the intravascular indwelling stent.

In the intravascular indwelling stent, the stent main body may be configured such that circular wires having repeated wavy bends along a circumferential direction of the intravascular indwelling stent are arranged in an extending direction of the intravascular indwelling stent, with the through-holes being located so as to fill gaps between the adjacent circular wires.

The intravascular indwelling stent allows the opening edges of through-holes as intimal formation initiation points to be substantially uniformly arranged over the entire stent main body. As a result, it is possible to reduce differences in progress of intimal formation that may occur due to uneven distribution of through-holes. In this way, the above-described effect of improving the blood flow conservation property of the branch blood vessel and the aneurysm opening portion embolization property can be inhibited from varying depending on arrangement of the intravascular indwelling stent in the blood vessel.

In the intravascular indwelling stent, the opening size of the through-hole may be 0.06 mm or more and 0.12 mm or less, the opening occupancy may be 30% or more and 35% or less, and the surface density of boundary may be 14/mm or more and 20/mm or less.

The intravascular indwelling stent improves the viability of the above-described effect of improving the blood flow conservation property of the branch blood vessel and the aneurysm opening portion embolization property.

Advantageous Effects of Invention

The intravascular indwelling stent according to the present invention improves both a blood flow conservation property of a branch blood vessel and an aneurysm opening portion embolization property.

DESCRIPTION OF EMBODIMENTS

Figure 1:
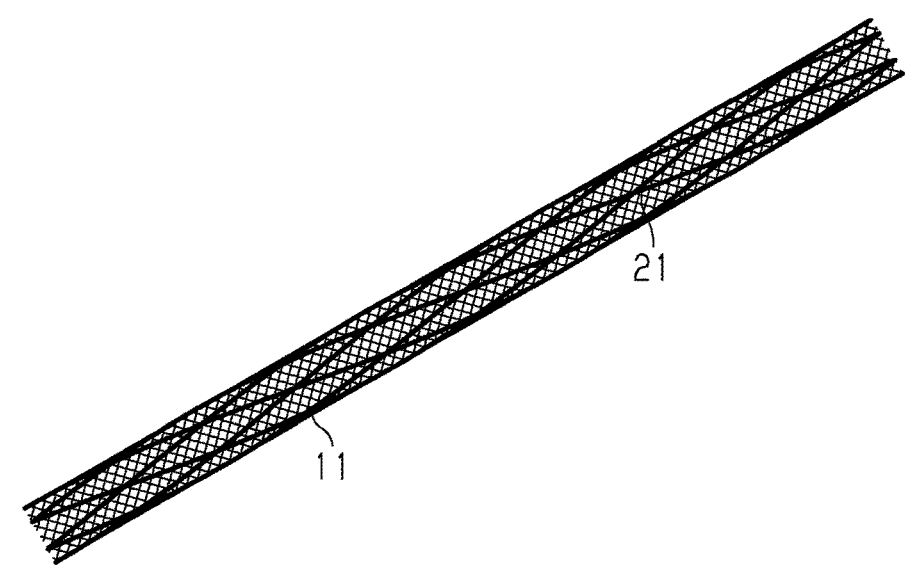
FIG. 1 is a side view showing the side structure of an intravascular indwelling stent during insertion of a catheter.
Figure 2:
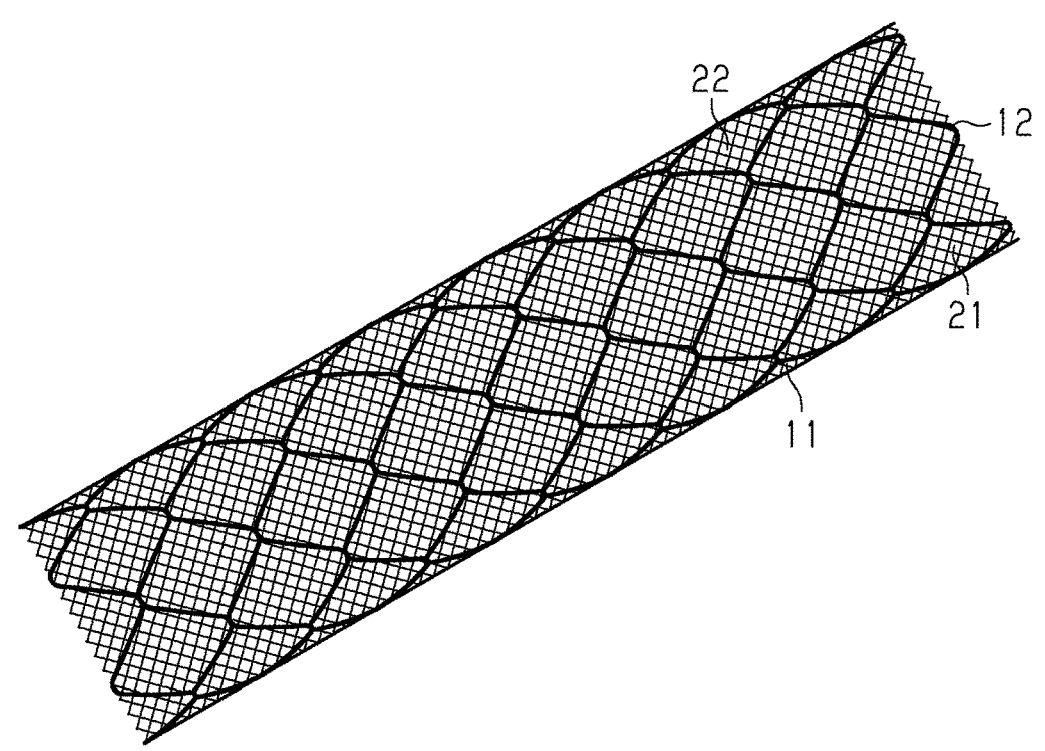
FIG. 2 is a side view showing the side structure of the intravascular indwelling stent after diameter expansion.
Figure 3:
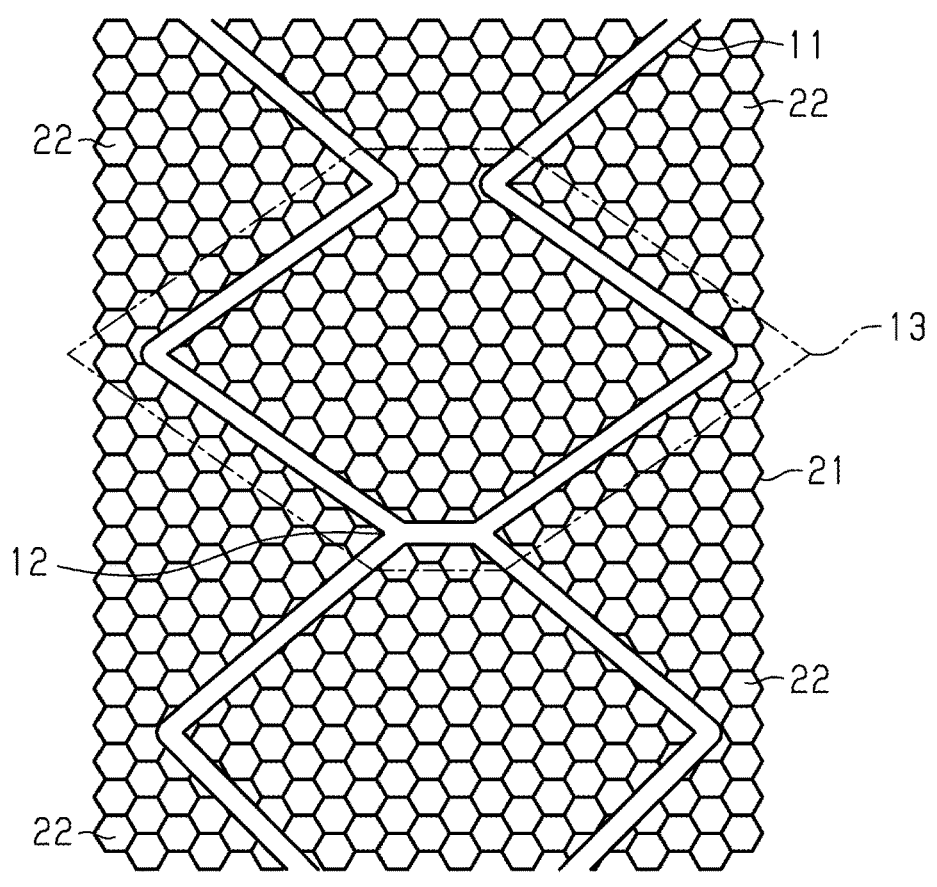
FIG. 3 is a side view showing an enlarged part of the intravascular indwelling stent after diameter expansion.

An embodiment of an intravascular indwelling stent will be described with reference to FIGS. 1 to 13. FIG. 1 is a side view showing the intravascular indwelling stent before diameter expansion, and FIG. 2 is a side view showing the intravascular indwelling stent mounted on a catheter. FIG. 3 is a side view showing an enlarged part of the side of the intravascular indwelling stent after diameter expansion.

[Intravascular Indwelling Stent]

The intravascular indwelling stent is applied to, for example, a stent graft for cerebral blood vessels or large arteries. The intravascular indwelling stent is disposed so as to cover the aneurysm opening portion of an aneurysm generated in the artery, and is used for clotting blood in the aneurysm.

As shown in FIG. 1, the intravascular indwelling stent includes a strut 11 as a stent main body which is diametrically expandable in the artery and has a cylindrical shape, and a cylindrical polymer film 21 held by the strut 11.

The strut 11 is a diametrically expandable metallic structure having a mesh shape. The length of the strut 11 in an extending direction is, for example, 10 mm or more and 300 mm or less before diameter expansion. The diameter of the strut 11 is, for example, 0.3 mm or more before diameter expansion. After diameter expansion, the diameter of the strut 11 is about 2 to 5 times the diameter before diameter expansion. The thickness of the strut 11 in a radial direction is 20 μm or more and 500 μm or less.

The structure of the strut 11 has a shape in which polygonal line-shaped circular wires having repeated bends in the circumferential direction of the strut 11 are arranged in the extending direction of the strut 11, with the circular wires being connected by a link. That is, the structure of the strut 11 has a link stent shape including unit structures 13 arranged in the circumferential direction of the strut 11 (see FIG. 3), and a link 12 connecting one of the adjacent unit structures 13 to the other in the extending direction of the strut 11 (see FIG. 2). The number of links is, for example, 2 or more and 24 or less in the circumferential direction of the strut 11.

The repeating unit structures 13 in the structure of the strut 11, which do not include the link, have a hexagonal shape and are arranged in the circumferential direction of the strut 11 and the extending direction of the strut 11. In the extending direction of the strut 11, one of the adjacent unit structures 13 and the other are connected by a link at a vertex of the hexagon.

The structure of the strut 11 may have a shape in which polygonal line-shaped circular wires having repeated wavy bends or curves along the circumferential direction of the strut 11 are arranged in the extending direction of the strut 11, with the circular wires being laser-welded or spray-welded to each other. That is, the structure of the strut 11 may be one that is free of links, with the circular wires being supported by the polymer film 21.

The structure of the strut 11 may be of coil type which is obtained by processing the circular wires into a coil shape. The coil type has low flexural rigidity in the extending direction of the strut 11 and is excellent in followability to the shape of a bent portion of the blood vessel.

The structure of the strut 11 may be of tube type which is obtained by laser processing or the like on a metal tube. The tube type has higher rigidity over the coil type in the radial direction of the strut 11, and is excellent in support of a blood vessel wall. Further, the structure of the strut 11 may separately include a member extending through the inside of the strut 11 along the extending direction of the strut 11.

The metallic material forming the strut 11 is, for example, stainless steel, titanium, tantalum, aluminum, tungsten, a nickel-titanium alloy, a cobalt-chromium alloy, a platinum-chromium alloy, or a cobalt-chromium-nickel-iron alloy, which is biocompatible. The metallic material forming the strut 11 is a material which is diametrically expanded by a balloon as an intravascular indwelling stent. The biocompatible metallic material is a material that is not decomposed in a living body or does not disappear in a living body, and does not trigger an allergic reaction or an inflammatory reaction.

The metallic material forming the strut 11 may be a shape memory material subjected to heat treatment so as to have self-expandability as an intravascular indwelling stent. The strut 11 is a laminated structure, and can include a core layer located at the center in a cross-section of the strut 11, and a covering layer that covers the entire outer surface of the core. The core layer and the covering layer are formed of mutually different metallic materials, and the covering layer is formed by, for example, thermal spraying in which metallic particles are sprayed to the core layer.

The polymer film 21 covers the entire strut 11 including the inside of the strut 11 and the outside of the strut 11. The polymer film 21 covering the outside of the strut 11 facilitates movement of the intravascular indwelling stent in the blood vessel. The polymer film 21 covering the outside of the strut 11 may be covered with a lubricant substance for further facilitating movement of the intravascular indwelling stent in the blood vessel. The lubricant substance is, for example, a hydrophilic small molecule such as glycerin, a biocompatible substance such as hyaluronic acid or gelatin, or a fat or oil component present in a living body.

The thickness of the polymer film 21 is, for example, 1 μm or more and 100 μm or less. When the thickness of the polymer film 21 is 1 μm or more, breakage of the polymer film in the process of forming the polymer film is prevented, whereby labor required for forming the polymer film 21 is reduced. When the thickness of the polymer film 21 is 100 μm or less, an increase in distance over which cells contained in the biological tissue material move is suppressed, whereby the connective tissue required for intimal formation from the intravascular indwelling stent is easily formed inside the intravascular indwelling stent.

The material forming the polymer film 21 is a polymeric elastomer which is biocompatible, and flexible enough to follow diameter expansion of the strut 11. The polymeric elastomer is, for example, a urethane polymer, a polyolefin polymer, a polystyrene polymer, a polyester polymer, a polyamide polymer, a silicone polymer, a fluorine polymer, a natural rubber polymer, or a copolymer or a polymer alloy thereof.

The material forming the polymer film 21 is, for example, a segmented urethane polymer. The segmented urethane polymer includes a flexible polyether moiety as a soft segment, and a moiety having an aromatic ring as a hard segment and a urethane bond, and has a microstructure in which the soft segment and the hard segment are phase-separated. The segmented urethane polymer imparts excellent antithrombogenicity and high strength and elongation to the polymer film 21 as compared to other materials.

The polymer film 21 may have a single-layer structure or a multilayer structure. The surface of the polymer film 21 may be covered with, for example, a biodegradable polymer that is degraded in a living body and in which degradation products do not have toxicity. Examples of the biodegradable polymer include polylactic acid, polyglycolic acid, poly-p-dioxanone, and poly-β-hydroxybutyric acid. The polymer film 21 having a biodegradable polymer on the surface thereof allows for early recovery of a vascular tissue from chronic inflammation caused by the polymer film 21.

The polymer film 21 includes a large number of through-holes 22 connecting the inside and the outside of the intravascular indwelling stent to each other, as shown in FIGS. 2 and 3. The through-holes 22 in the polymer film 21 each have, for example, a substantially hexagonal shape. The through-holes 22 in the polymer film 21 are located in gaps separated by the unit structures 13 of the strut 11, and are located so as to fill the gaps between the circular wires adjacent in the extending direction of the intravascular indwelling stent. That is, the polymer film 21 does not expose the strut 11 to the outside, and connects the inside and the outside of the cylinder in the intravascular indwelling stent to each other substantially uniformly over the entire intravascular indwelling stent.

The shape of the opening of each through-hole 22 can be changed to a circular shape, an elliptical shape, a triangular shape, a quadrangular shape, a pentagonal shape, or an irregular shape other than these geometric shapes. The position of each through-hole 22 is, for example, a grid point on various geometric grids developed on a cylindrical surface such as a grid point on an orthorhombic grid, a grid point on a hexagonal grid, a grid point on a square grid, a grid point on a rectangular grid, or a grid point on a parallel grid. The opening size of the through-hole 22 is a diameter of the largest circle inscribed in the opening at two or more points.

When the strut 11 is of coil type or has a structure with a link, similarly the through-holes 22 in the polymer film 21 do not expose the strut 11 to the outside, and causes the inside and the outside of the cylinder in the intravascular indwelling stent to communicate with each other. That is, the through-holes 22 in the polymer film 21 are located in gaps between the circular wires adjacent in the extending direction of the strut 11 or in gaps separated by the circular wires adjacent in the extending direction of the strut 11 and the link.

The polymer film 21 can also contain a drug eluting into blood as long as the size of the through-holes 22 can be maintained. The drug contained in the polymer film 21 is, for example, a drug that promotes an aneurysm embolizing effect, a drug that promotes integration of the aneurysm into an organ, a drug that prevents delayed stent thrombosis, or an immunosuppressive drug. The drug contained in the polymer film 21 is, for example, heparin, an antithrombin drug, a platelet membrane receptor antibody, recombinant hirudin, a vascular tensin convertase inhibitor, a vascular endothelial growth factor, a fibroblast growth factor antagonist, steroid, a serotonin blocking antibody, or histamine.

In a method for producing an intravascular indwelling stent, for example, a cylindrical mandrel is immersed in a polymer solution for forming a polymer film 21, thereby forming a polymer membrane on the outer peripheral surface of the mandrel. In this way, an inner film that covers the inside of the strut 11 in the polymer film 21 is formed. Subsequently, the strut 11 is brought into close contact with the outside of the inner film formed on the outer peripheral surface of the mandrel, whereby the inner film is bonded to the inside of the strut 11.

Next, the mandrel including the inner film and the stent main body are immersed again in the polymer solution for forming the polymer film 21, thereby forming a polymer membrane outside the strut 11, with the polymer membrane integrated with the inner film. In this way, the polymer film 21 covering the entire strut 11 is formed.

Next, the polymer film 21 covering the inside and the outside of the strut 11 and the strut 11 are extracted from the mandrel, and by laser processing, the polymer film 21 covering the strut 11 is provided with through-holes 22 extending through the polymer film 21. In this way, the entire strut 11 is covered with the polymer film 21 provided with the through-holes 22, so that an intravascular indwelling stent is produced.

Alternatively, it is also possible to perform laser processing before extraction from the mandrel, and in this case, the polymer film 21 and the strut 11 are extracted from the mandrel after the laser processing to produce an intravascular indwelling stent.

In a method for delivering a stent using an intravascular indwelling stent, for example, the intravascular indwelling stent is diametrically contracted with respect to the initial shape, and inserted into the lumen of a blood vessel by a catheter. When the intravascular indwelling stent is of balloon type, the intravascular indwelling stent is pressed against the inner peripheral surface of the blood vessel by diametrically expanding the intravascular indwelling stent by use of a balloon. The catheter for transfer is pulled out from the intravascular indwelling stent to indwell the diametrically expanded intravascular indwelling stent in the lumen of the blood vessel. When the intravascular indwelling stent is self-expandable, the intravascular indwelling stent is released from the catheter for transfer to automatically diametrically expand the intravascular indwelling stent.

The diametrically expanded shape of the intravascular indwelling stent may be an initial shape of the intravascular indwelling stent or may be a shape different from the initial shape. When the diametrically expanded shape of the intravascular indwelling stent is the initial shape of the intravascular indwelling stent, development of the diametrically expanded shape in the lumen is stabilized, and it is possible to reduce strain and residual stress in the diametrically expanded shape.

It is possible to change the configuration so that the polymer film 21 is located only inside the strut 11 or outside the strut 11. Further, it is possible to produce the polymer film 21 by winding the polymer film 21 around the strut 11 or winding the strut 11 around the polymer film 21.

The through-holes 22 in the polymer film 21 can be changed so as to expose a part of the strut 11 to the outside. In this case, the through-holes 22 expose a part of the strut 11 in a portion corresponding to the blood vessel wall in the polymer film.

[Through-Holes 22]

The configuration of the through-holes 22 will now be described with reference to FIGS. 4 to 12. First, environmental situations around an artificial material such as an intravascular indwelling stent when the artificial material is indwelled in the blood vessel will be described, followed by a description of factors of intimal formation to which through-holes 22 contribute, and then various conditions satisfied by the through-holes 22.

Figure 4:
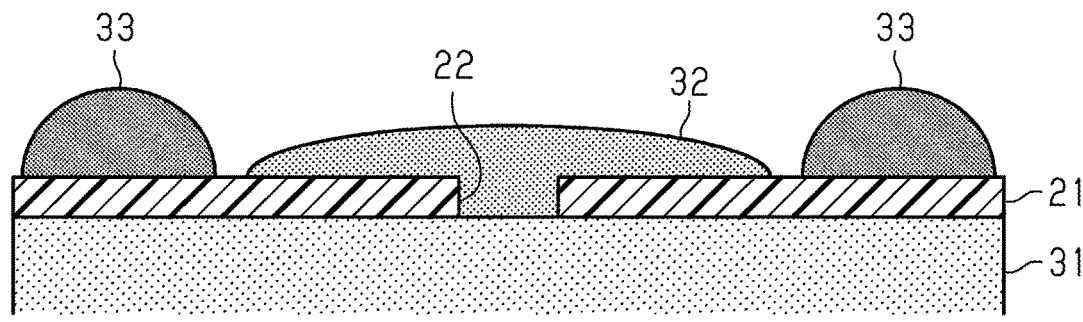
FIG. 4 is a schematic diagram showing the process of forming a connective tissue in a small hole formed in an artificial material.

FIG. 4 shows an example in which an intravascular indwelling stent having a small number of through-holes 22 having a small opening size, i.e. (a) an intravascular indwelling stent having a small number of small holes is indwelled in a blood vessel.

Figure 5:
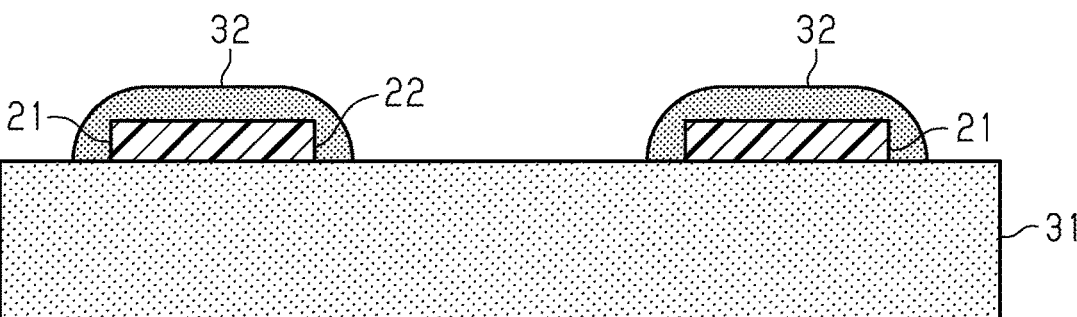
FIG. 5 is a schematic diagram showing the process of forming a connective tissue in a large hole formed in an artificial material.
Figure 6:
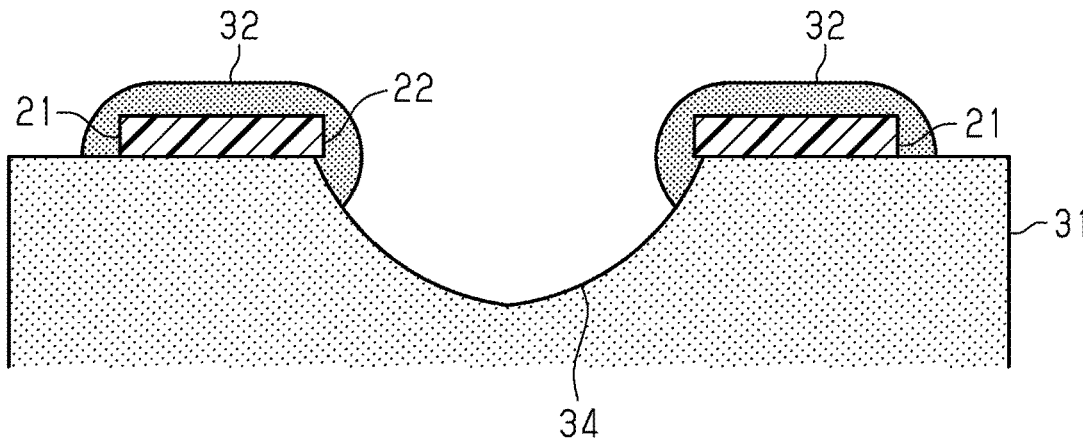
FIG. 6 is a schematic diagram showing the process of forming a connective tissue in a large hole disposed in an aneurysm opening portion.

FIGS. 5 and 6 show an example in which an intravascular indwelling stent having a large number of through-holes 22 having a large opening size, or an intravascular indwelling stent having a small number of through-holes 22 having a large opening size, i.e. (b) an intravascular indwelling stent having large holes is indwelled in a blood vessel.

Figure 7:
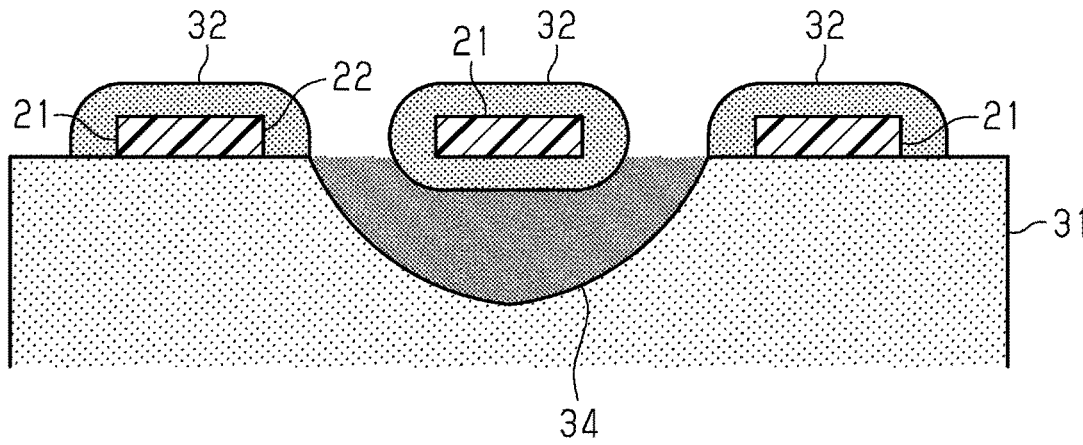
FIG. 7 is a schematic diagram showing the process of forming a connective tissue in a small hole disposed in an aneurysm opening portion.
Figure 8:
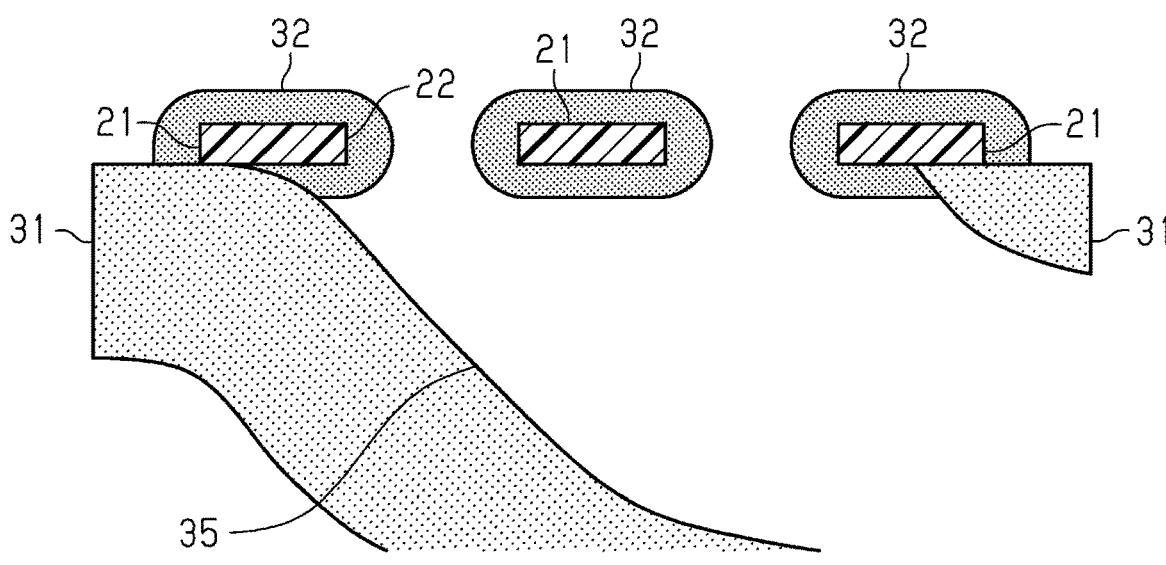
FIG. 8 is a schematic diagram showing the process of forming a connective tissue in a small hole disposed in a branch blood vessel.

FIGS. 7 and 8 show an example in which an intravascular indwelling stent having a large number of through-holes 22 having a small opening size, i.e. (c) an intravascular indwelling stent having a large number of small holes is indwelled in a blood vessel.

In general, when an artificial material is indwelled in a blood vessel, platelets and the like are immediately attached to or aggregated on the surface of the artificial material, resulting in formation of a blood clot on the surface of the artificial material. For suppressing blood clot formation due to indwelling of an artificial material in a blood vessel, an anticoagulant such as heparin or an antiplatelet drug for preventing blood coagulation caused by a thrombin action is normally used when the artificial material is indwelled in the blood vessel. The period over which the anticoagulant or the antiplatelet drug is administered is longer than or equal to a period required for forming the artificial material into an intima in the blood vessel, and is, for example, six months to one year when the surface area of the artificial material is small, and is even longer or may last throughout life when the surface area of the artificial material is large.

Cells that contribute to intimal formation move from an intima 31 of the blood vessel to the surface of the polymer film 21 through through-holes 22 when the intravascular indwelling stent is indwelled in a blood vessel as shown in FIG. 4. The cells that contribute to intimal formation form a connective tissue on the hole inner surfaces that define the respective through-holes 22 and the surface exposed in the blood vessel in the polymer film 21, so that intimal formation is completed.

(a) Intravascular Indwelling Stent Having Small Number of Small Holes

The larger the surface area of the polymer film 21, the longer the period for a connective tissue 32 to cover the polymer film 21, i.e. the period until completion of intimal formation. When the period until completion of intimal formation is long, the opening of the through-hole 22 is gradually closed by the connective tissue, and therefore even though intimal formation on the hole inner surface of the through-hole 22 is completed, a portion which is not covered with the connective tissue still remains on the surface of the polymer film 21.

That is, if the surface of the polymer film 21 is excessively large in area, the surface of the polymer film 21 on the inner side of the blood vessel has a portion that is not covered with the connective tissue 32 not only when the through-hole 22 is closed by the connective tissue 32 but also when a part of the through-hole 22 is closed by the connective tissue 32. Blood is likely to be attached to such a portion. As a result, administration of an anticoagulant drug or an antiplatelet drug has to be continued for a long period of time so that a blood clot 33 is not formed on the surface of the polymer film 21. After all, in an intravascular indwelling stent having a small number of small holes, the period for administration of an anticoagulant drug or an antiplatelet drug becomes longer because the surface of the polymer film 21 is excessively large in area.

(b) Intravascular Indwelling Stent Having Large Holes

As shown in FIG. 5, the larger the opening size of the through-hole 22, the shorter the period for the connective tissue 32 to cover the polymer film 21, i.e. the period until completion of intimal formation. Even through the opening of the through-hole 22 is gradually closed by the connective tissue 32, the surface of the polymer film 21 is completely covered with the connective tissue 32 to complete intimal formation throughout the intravascular indwelling stent at the time of completing intimal formation at the hole inner surfaces defining the respective through-holes 22.

Such a tendency of good intimal formation is more feasible as the number of the through-holes 22 of the intravascular indwelling stent increases, i.e. the surface area of the polymer film 21 decreases, and in an intravascular indwelling stent having large holes, there is the same tendency even if the number of the through-holes is small. As a result, in an intravascular indwelling stent having large holes, intimal formation from the polymer film 21 is accelerated and the thickening of a neointima is further suppressed. In the intravascular indwelling stent having large holes, it is possible to prevent continuous administration of an anticoagulant drug or an antiplatelet drug over a long period of time.

However, if the intravascular indwelling stent having large holes is disposed at the aneurysm opening portion of an aneurysm 34 as shown in FIG. 6, the opening of the through-hole 22 is still wide open at the time of completion of intimal formation from the polymer film 21, and embolization at the aneurysm opening portion is insufficient. After all, in the intravascular indwelling stent having large holes, it is possible to accelerate intimal formation, but it is difficult to obtain an aneurysm opening portion embolization property because the opening size of the through-hole 22 is excessively large.

(c) Intravascular Indwelling Stent Having Large Number of Small Holes

As shown in FIG. 7, in an intravascular indwelling stent having a large number of small holes, the area of the surface to be covered with the connective tissue 32 decreases because there are a large number of through-holes 22 although the opening size of the through-hole 22 is small as in (a) the intravascular indwelling stent having a small number of small holes. It is possible to accelerate intimal formation as in (b) the intravascular indwelling stent having large holes. The opening of the through-hole 22 is gradually closed by the connective tissue 32, so that the entire surface of the polymer film 21 is covered with the connective tissue 32 when intimal formation at the inner peripheral surface defining the through-hole 22 is completed.

As a result, in the intravascular indwelling stent having a large number of small holes, it is possible to accelerate intimal formation from the polymer film 21, further suppress thickening of a neointima, and prevent continuous administration of an anticoagulant drug or an antiplatelet drug over a long period of time, as in an intravascular indwelling stent having large holes. When intimal formation from the polymer film 21 is completed, a part of the through-hole 22 is closed by the connective tissue 32 to the extent that blood flow is stagnated in the aneurysm, and it is possible to embolize the aneurysm opening portion. Therefore, in the intravascular indwelling stent having a large number of small holes, an aneurysm opening portion embolization property is obtained while intimal formation is accelerated.

There are not a few symptoms in which as described above, the branch blood vessel 35 extends from a body part of the aneurysm 34 as in an aneurysm generated at a branch portion between the internal carotid artery and the posterior communicating artery as shown in FIG. 8. Among intravascular indwelling stents having a large number of small holes as described above, in which the aneurysm opening portion embolization property is obtained while intimal formation is accelerated, those ensuring that the branch opening of the branch blood vessel 35 is not embolized are required. That is, a configuration of through-holes 22 is required which ensures that the aneurysm opening portion embolization property is obtained and a blood flow conservation property of the branch blood vessel 35 is obtained while intimal formation is accelerated.

(d) Opening Occupancy

As described above, the opening occupancy as an area of openings per unit area is an indication of the magnitude of an area that should be covered with the connective tissue not later than completion of intimal formation. In other words, the opening occupancy of the through-holes 22 serves as an indication of the magnitude of the surface area of the polymer film 21 to be formed into an intima, and as an indication of ease of passage of the biological tissue material (iii) through the openings of the through-holes 22.

A reaction in which an intravascular indwelling stent formed of an artificial material and a biological tissue material are directly involved is important in an initial stage where the biological tissue material recognizes the intravascular indwelling stent as a foreign substance. A reaction that occurs first when the intravascular indwelling stent and the biological tissue material come into contact with each other is adsorption of protein, adsorptive replacement, attachment of cells, or the like, and is not determined only by ease of passage of protein and cells.

That is, the opening occupancy is not deeply involved in ease of exhibiting a self-defense function (iv) by the biological tissue material. Therefore, in a configuration of through-holes 22 which is determined only on the basis of ease of passage of the biological tissue material in through-holes 22, in other words, a configuration of through-holes 22 which are determined only on the basis of the opening occupancy, there may be a large difference between a process at an aneurysm opening portion after indwelling and a predicted process. Similarly, there may be a large difference between a process at a branch opening after indwelling and a predicted process.

Moreover, between the aneurysm opening portion where the blood flow is likely to stagnate and the branch opening of the branch blood vessel 35 where the blood continues to flow, there is a significant difference in period required for cells to move to the surface of the artificial material. In a configuration of through-holes 22 which is determined on the basis of treating the factor of intimal formation at the aneurysm opening portion (i) and the factor of intimal formation at the branch opening (ii) as equivalents, there may be a larger difference between a process at the aneurysm opening portion after indwelling and a predicted process. Similarly, there may be a further large difference between a process at the branch opening after indwelling and a predicted process.

(e) Surface Density of Boundary

In the course of extensively conducting studies on a process in which the intravascular indwelling stent is covered with a biological tissue material, the inventors of the present application have found that formation of a connective tissue covering the intravascular indwelling stent starts to occur with opening edges of through-holes 22 as formation initiation points. That is, the inventors have found that a foreign substance recognition reaction and an encapsulation reaction resulting from contact of the biological tissue material with an artificial material proceed with the opening edges of the through-holes 22 as the formation initiation points. In other words, the inventors have found that production of collagen is started with the opening edges of the through-holes 22 as the formation initiation points, so that the connective tissue spreads from the opening edge of the through-hole 22 to the entire surface of the polymer film. The inventors have found that the connective tissue, beginning to be formed with the opening edges of the through-holes 22 as the formation initiation points, grows to cover the surface of the polymer film 21 that separates the through-holes 22 from each other, whereby the polymer film 21 is formed into an intima.

In the process of the intimal formation described above, the length of the opening edges defining the through-holes 22 and, moreover, the surface density of boundary obtained by normalizing the length of the opening edges defining the through-holes 22 per unit area mean the size of a formation initiation point where intimal formation starts within the unit area. In other words, the surface density of boundary of through-holes 22 serves as an indication of ease of exhibiting a self-defense function (iv) by the biological tissue material, and also as indication of ease of progress of intimal formation in the aneurysm opening portion (i) and the branch opening (ii).

Figure 9:
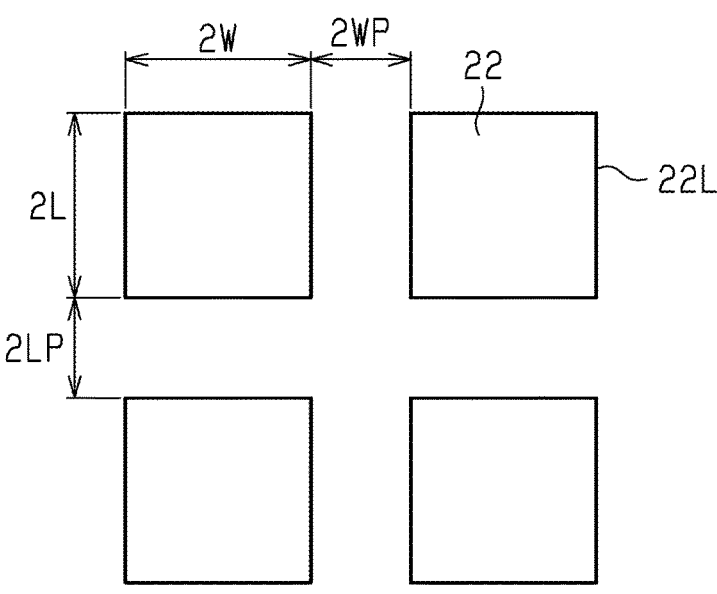
FIG. 9 is a plan view for illustrating the definition of a surface density of boundary.

FIG. 9 is a plan view for illustrating an opening size, an opening occupancy, and a surface density of boundary, and shows an example in which square openings, as an example of openings of the through-holes 22, are arranged in two rows and two columns in which the centers of the openings are each arranged at a grid point on a square grid.

As shown in FIG. 9, the opening of the through-hole 22 is a square region, and is arranged such that the center of the opening substantially coincides with the grid point of the square grid. The length of each opening in the extending direction of the strut 11 is an opening size $2L$ which is a length of one side of the opening. The direction orthogonal to the extending direction of the strut 11 is a circumferential direction of the strut 11. The length of each opening in the circumferential direction of the strut 11 is an opening size $2W$ which is a length of the other side of the opening.

The openings are spaced by an inter-opening size $2LP$ in the extending direction of the strut 11. The inter-opening size $2LP$ is an example of a length between adjacent through-holes 22, and is the shortest distance between the openings adjacent in the extending direction of the strut 11. The openings are spaced by an inter-opening size $2WP$ in the circumferential direction of the strut 11. The inter-opening size $2WP$ is also an example of a length between adjacent through-holes 22, and is the shortest distance between the openings adjacent in the circumferential direction of the strut 11.

The distance between the centers of openings in the through-holes 22 is the sum of the opening size $2L$ and the inter-opening size $2LP$, and is the sum of the opening size $2W$ and the inter-opening size $2WP$.

The area of the unit region on the outer surface of the strut 11 is a unit area of the strut 11. The total area of the openings in the unit region is an opening area defined by the openings. The ratio of the opening area to the unit area of the strut 11 is an opening occupancy (%). The sum of the lengths of boundary lines 22L present in the unit region is a surface density of openings. The value obtained by dividing the surface density of openings by the unit area of the strut 11 is a surface density of boundary (/mm).

The unit region on the outer surface of the strut 11 is, for example, a region occupied by the unit structures 13 which are repeating units on the outer surface. The unit region on the outer surface of the strut 11 may be a region including a group of openings and a periphery thereof, or may be a preset rectangular region. When the unit region is a predetermined region that is repeated independently of the opening, the above-described opening occupancy and surface density of boundary are an average value of opening occupancies in all the unit regions and an average value of surface densities of boundary in all the unit regions, respectively.

As described above, the opening occupancy (d) serves as an indication of ease of passage of the biological tissue material through the openings of the through-holes 22. On the other hand, the surface density of boundary (e) serves as an indication of ease of exhibiting a self-defense function by the biological tissue material. The opening occupancy (d) and the surface density of boundary (e) are factors deeply involved in the process of intimal formation, and a configuration of through-holes 22 which is determined on the basis of these factors reduces a difference generated between a process after indwelling and a predicted process.

Figure 10:
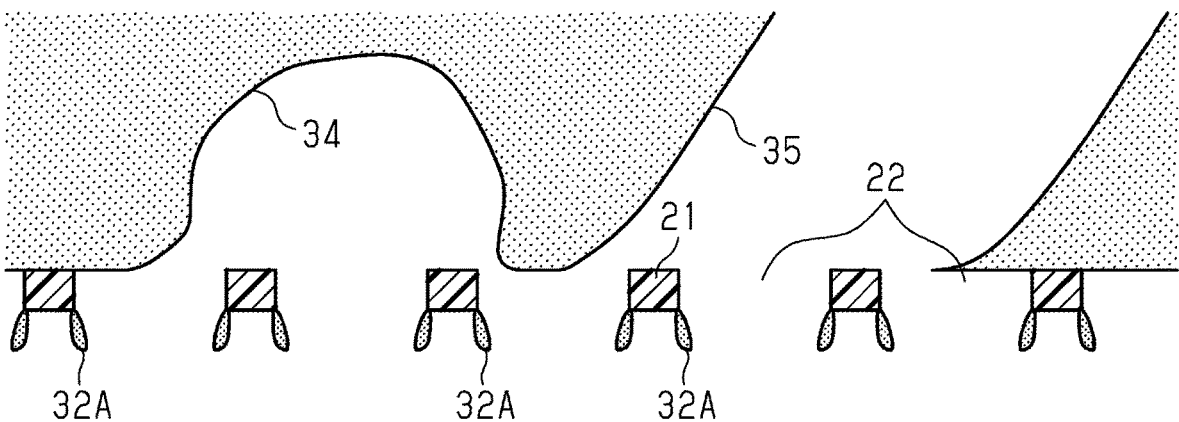
FIG. 10 is a schematic diagram showing the state in which collagen is produced at an opening edge of a through-hole.

However, between the aneurysm opening portion of the aneurysm 34 where the blood flow is likely to stagnate and the branch opening of the branch blood vessel 35 where the blood continues to flow, there is a significant difference in period required for cells to move to the opening edge of the through-hole 22 as shown in FIG. 10. The periods until the start of production of collagen 32A with the opening edges of the through-holes 22 as the formation initiation points are also different.

That is, the environment contributing to intimal formation at the aneurysm opening portion and the environment contributing to intimal formation at the branch opening are different from each other, and therefore the degrees of contribution of the factor of intimal formation at the aneurysm opening portion (i) and the factor of intimal formation at the branch opening (ii) are also different from each other. Therefore, a configuration of through-holes 22 in which the aneurysm opening portion embolization property is obtained and the blood flow conservation property of the branch blood vessel 35 is also obtained is difficult to determine from only the factor of intimal formation at the aneurysm opening portion (i) or only the factor of intimal formation at the branch opening (ii).

For example, for ensuring both patency of the branch blood vessel 35 and intimal formation there, increasing the opening occupancy to facilitate flow of blood is effective, but this approach alone is insufficient, and it is necessary that intimal formation from the polymer film 21 proceed even in an environment where the blood continues to flow. That is, it is necessary that the surface density of boundary be determined so as to perform intimal formation sufficient to ensure that production of collagen proceeds even in an environment where cells contained in the biological tissue material are less likely to be attached to the surface of the artificial material, and flow of blood is ensured.

For example, for ensuring both embolization of the aneurysm 34 and intimal formation there, reducing the opening occupancy to resist flow of blood is effective, but this approach is radical for additionally ensuring patency of the branch blood vessel 35, and it is preferable that embolization of the aneurysm 34 be achieved by partial embolization after the polymer film 21 is formed into an intima. That is, it is necessary to determine the surface density of boundary so that embolization subsequently occurs by partial closing of through-holes 22 after intimal formation in an environment where cells contained in the biological tissue material move easily to the surface of the artificial material.

Thus, of the polymer film 21 forming the outer surface of the intravascular indwelling stent, a portion that is in direct contact with the vascular intima and a portion located at the aneurysm opening portion where the blood flow stagnates in the vicinity of the vascular intima are portions where cells contained in the biological tissue material move easily, and in this portion of the polymer film 21, intimal formation proceeds relatively easily. On the other hand, a portion of the polymer film 21, which is located at the branch opening through which blood continues to flow, is a portion to which cells contained in the biological tissue material are less likely to be attached, and in this portion of the polymer film 21, intimal formation relatively hardly proceeds.

The inventors of the present application have classified the aneurysm opening portion (i) of the aneurysm 34 as a type in which intimal formation proceeds relatively easily while classifying the branch opening (ii) of the branch blood vessel 35 as a type in which intimal formation relatively hardly proceeds. On the basis of tests on the types, conditions achieving both the aneurysm opening portion embolization property and the blood flow conservation property at the branch opening have been specified as follows.

(Condition 1) The opening size at diameter expansion is 0.02 mm or more and 0.2 mm or less.

(Condition 2) The opening occupancy at diameter expansion is 25% or more and 41% or less.

(Condition 3) The surface density of boundary at diameter expansion is 9.5/mm or more and 30/mm or less.

The minimum value of the opening size which enables passage of a biological tissue material for forming a connective tissue is about 0.01 mm. Therefore, when the opening size is 0.02 mm or more, the biological tissue material for forming a connective tissue sufficiently passes through the through-hole 22.

When the opening size is 0.02 mm or more, the opening occupancy is 25% or more, and the surface density of boundary is 9.5/mm or more and 30/mm or less, a situation in which it is difficult to obtain a closing property at the aneurysm opening portion (i) of the aneurysm 34 due to an increase in opening size and opening occupancy is prevented by specifying the surface density of boundary. When the opening size is 0.02 mm or more, the opening occupancy is 25% or more, and the surface density of boundary is 9.5/mm or more and 30/mm or less, a situation in which it is difficult to obtain the blood flow conservation property at the branch opening (ii) of the branch blood vessel 35 due to a decrease in surface density of boundary is prevented by specifying the opening occupancy.

When the opening size is 0.02 mm or more, the opening occupancy is 41% or less, and the surface density of boundary is 9.5/mm or more and 30/mm or less, a situation in which it is difficult to obtain the closing property at the aneurysm opening portion (i) of the aneurysm 34 due to an increase in opening size is prevented by specifying the opening occupancy and the surface density of boundary.

When the opening size is 0.2 mm or less, the opening occupancy is 25% or more, and the surface density of boundary is 9.5/mm or more, a situation in which it is difficult to obtain the closing property at the aneurysm opening portion (i) of the aneurysm 34 due to an increase in opening occupancy is prevented by specifying the opening size and the surface density of boundary. When the opening size is 0.2 mm or less, the opening occupancy is 25% or more, and the surface density of boundary is 9.5/mm or more, a situation in which it is difficult to obtain the blood flow conservation property at the branch opening (ii) of the branch blood vessel 35 due to a decrease in opening size and an increase in surface density of boundary is prevented by specifying the opening occupancy.

When the opening size is 0.2 mm or less, the opening occupancy is 41% or less, and the surface density of boundary is 9.5/mm or more, a situation in which it is difficult to obtain the blood flow conservation property at the branch opening (ii) of the branch blood vessel 35 due to a decrease in opening size and a decrease in opening occupancy is prevented by specifying the surface density of boundary.

Thus, an intravascular indwelling stent that satisfies conditions 1, 2 and 3 described above improves the blood flow conservation property of the branch blood vessel and the aneurysm opening portion embolization property because the opening size is 0.02 mm or more and 0.2 mm or less, the opening occupancy is 25% or more and 41% or less, and the surface density of boundary is 9.5/mm or more and 30/mm or less.

The intravascular indwelling stent is required to have strength sufficient to support a blood vessel wall, and have flexibility sufficient to follow bending of the blood vessel. Further, the intravascular indwelling stent is also required to have stress such that the blood vessel wall is pressed outward with a uniform pressure. Thus, determining the opening occupancy (d) and the surface density of boundary (e) so as to satisfy conditions 1, 2 and 3 in the intravascular indwelling stent required to have various mechanical properties considerably restricts structural freedom in the intravascular indwelling stent.

Thus, in a configuration in which through-holes 22 include through-holes 22 having different opening sizes, it is possible to set a small opening size at a site required to have strength sufficient to support a blood vessel wall and set a large opening size at a site required to have flexibility. Further, since the opening size of each through-hole 22 in the diametrically contracted intravascular indwelling stent is allowed to change to various sizes after diameter expansion, it is also possible to increase the degree of freedom of design in the intravascular indwelling stent in this respect.

Test Example A

Figure 11:
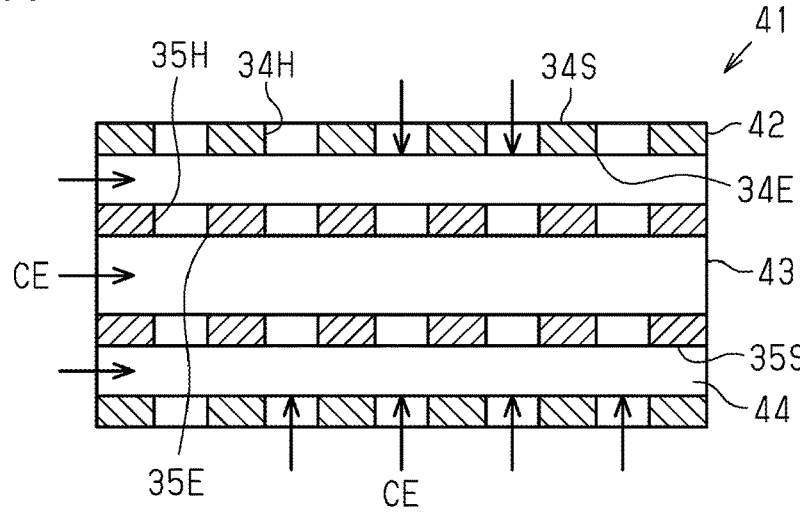
FIG. 11 is a cross-sectional view showing the cross-sectional structure of a connective tissue testing device used in a test example.
Figure 12:
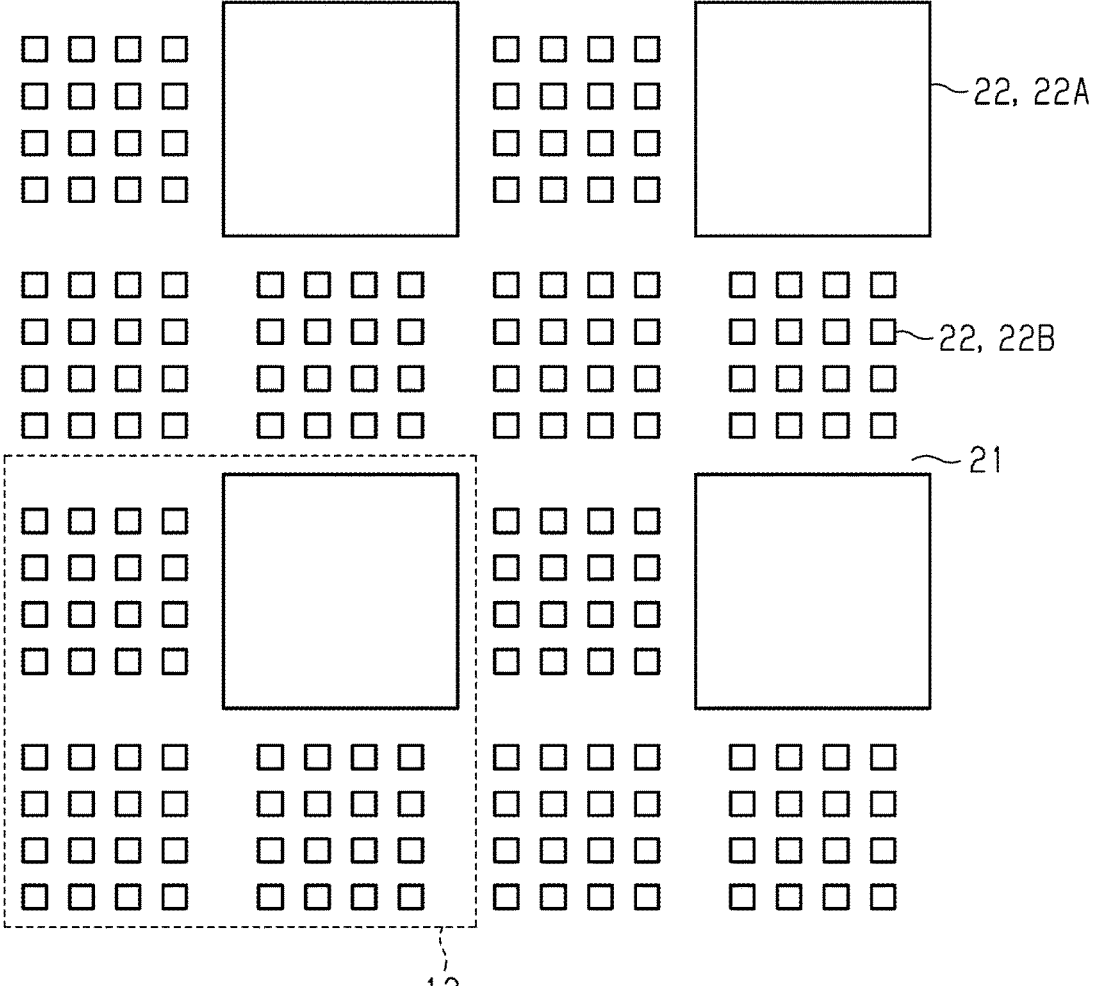
FIG. 12 is a plan view showing an example of a through-hole used in a test example.

Test examples performed to specify conditions 1, 2 and 3 described above will be described with reference to FIGS. 11 and 12. FIG. 11 is a cross-sectional view showing a cross-sectional structure of a connective tissue testing device used in the test examples. FIG. 12 is a graph showing the relationship between the state of a connective tissue and an opening occupancy and a surface density of boundary in each test example.

As shown in FIG. 11, a connective tissue testing device 41 includes a resin outer cylinder 42 and a resin inner cylinder 43.

The outer cylinder 42 is a cylindrical body having a cylindrical shape. The inner diameter of the outer cylinder 42 is 5 mm, and the thickness of the outer cylinder 42 is 0.5 mm. The outer cylinder 42 includes large number of outer cylinder through-holes 34H having openings in an outer peripheral surface 34S. The outer cylinder through-hole 34H extends through the outside and the inside of the outer cylinder 42. As an example, the outer cylinder through-hole 34H is located at each grid point on a square grid defined along the outer peripheral surface 34S. The outer cylinder through-hole 34H is a quadrangular hole having a square opening or a circular hole having a circular opening. As another example, the outer cylinder through-hole 34H is a hexagonal hole which has a regular hexagonal opening or a circular hole which has a circular opening and which is located at each grid point on a rhombic grid defined along the outer peripheral surface 34S. Another example of the outer cylinder through-hole 34H includes a large hole which is located at each grid point on a square grid defined along the outer peripheral surface 34S and has a square opening, and a small hole which is located at each grid point on a square grid having a grid constant smaller than that of the foregoing square grid so as to fill a gap between adjacent large holes and has a square opening.

The inner cylinder 43 is a cylindrical body having a cylindrical shape. A part of the outer peripheral surface of the inner cylinder 43 is fixed to the inner peripheral surface of the outer cylinder 42 by a bridge portion 44. That is, a gap having a predetermined width is formed between the outer peripheral surface of the inner cylinder 43 and the inner peripheral surface of the outer cylinder 42, and the inner cylinder 43 is fixed to the outer cylinder 42 such that the gap is opened at both ends of the connective tissue testing device 41. The inner cylinder 43 has an inner diameter of 2 mm, and the inner cylinder 43 has a thickness of 0.5 mm. The inner cylinder 43 is fixed to the inner peripheral surface of the outer cylinder 42 such that the diameter-direction width of the gap between the outer peripheral surface 35S of the inner cylinder 43 and the inner peripheral surface of the outer cylinder 42 is 1 mm.

The inner cylinder 43 includes a large number of inner cylinder through-holes 35H having openings in the outer peripheral surface 35S. The inner cylinder through-hole 35H extends through the outside and the inside of the inner cylinder 43. As an example, the inner cylinder through-hole 35H is located at each grid point on a square grid defined along the outer peripheral surface 35S. The inner cylinder through-hole 35H is a quadrangular hole having a square opening or a circular hole having a circular opening. As another example, the inner cylinder through-hole 35H is a hexagonal hole which has a regular hexagonal opening or a circular hole which has a circular opening and which is located at each grid point on a rhombic grid defined along the outer peripheral surface 35S. Another example of the inner cylinder through-hole 35H includes a large hole which is located at each grid point on a square grid defined along the outer peripheral surface 35S and has a square opening, and a small hole which is located at each grid point on a square grid having a grid constant smaller than that of the foregoing square grid so as to fill a gap between adjacent large holes and has a square opening.

The connective tissue testing device 41 is embedded in a subcutaneous pocket in the abdomen of a dog as an environment in which the biological tissue material exists. Here, for forming a subcutaneous pocket, a minimum incision is performed on the living body under sufficient anesthesia. Subsequently, a guide rod having a convex curved shape at a tip thereof is inserted into the living body from an insertion opening on the surface of the living body, and a circular tube-shaped insertion tube is inserted into the living body from the insertion opening while the outer peripheral surface of the guide rod is slid. Subsequently, the guide rod is pulled out from the inside of the insertion tube, and the connective tissue testing device is then inserted to the tip of the insertion tube while the inner peripheral surface of the insertion tube is slid. The insertion tube is pulled out from the insertion opening while a pushing rod is inserted into the insertion tube to hold the position of the connective tissue testing device, and the pushing rod is further pulled out to indwell the connective tissue testing device in the living body, so that the insertion opening as a wound site is closed.

The connective tissue testing device 41 embedded in an environment where the biological tissue material is present is taken out from the environment after the elapse of a predetermined embedment period which is a period during which the connective tissue is formed. When the connective tissue testing device 41 is taken out from the living body, minimum incision is first performed on the living body under sufficient anesthesia. After the connective tissue testing device 41 is taken out, the wound site is closed.

In the connective tissue testing device 41 embedded in the living body, the outer peripheral surface of the outer cylinder 42, both end surfaces of the outer cylinder 42, and both end surfaces of the inner cylinder 43 are in direct contact with the biological tissue material. In the connective tissue testing device 41, first, a cell CE directly moves from the biological tissue material to the outer cylinder through-hole 34H, a connective tissue is formed on the inner peripheral surface of the outer cylinder 42 through the outer cylinder through-hole 34H, and the biological tissue material enters between the inner peripheral surface of the outer cylinder 42 and the outer peripheral surface 35S of the inner cylinder 43 through the outer cylinder through-hole 34H. The cell CE moves toward the outer peripheral surface 35S of the inner cylinder 43, the inner peripheral surface and the inside of the inner cylinder through-hole 35H from the end surface of the inner cylinder 43 that is in direct contact with the biological tissue material. A connective tissue body is formed on the inner peripheral surface and the outer peripheral surface 35S of the inner cylinder 43. Here, the outer cylinder 42 is recognized as a foreign substance, and collagen is produced from an opening edge 34E of the outer cylinder through-hole 34H. Subsequently, an opening edge 35E of the inner cylinder through-hole 35H is recognized as a foreign substance by the cell having moved to the outer peripheral surface 35S and the inner peripheral surface of the inner cylinder 43, and collagen is also produced from the opening edge 35E of the inner cylinder through-hole 35H.

At the branch opening of the branch blood vessel 35, the cell CE moves from the periphery of the branch opening, and the cell reaches the opening edge of the through-hole 22 to form a connective tissue. Formation of a connective tissue which requires movement of the cell CE to the opening edge 35E of the inner cylinder through-hole 35H from the end surface of the inner cylinder 43 that is in direct contact with the biological tissue material resembles formation of the connective tissue in the through-hole 22 located at the branch opening of the branch blood vessel 35.

That is, as a test simulating an environment in which intimal formation proceeds relatively easily, such as the aneurysm opening portion (i) of the aneurysm 34, first, outer cylinder through-holes 34H were provided. Subsequently, as a test simulating an environment in which intimal formation relatively hardly proceeds, such as the branch opening (ii) of the branch blood vessel 35, the outer cylinder 42 having outer cylinder through-holes 34H that are large enough to be prevented from being closed by the connective tissue, and inner cylinder through-holes 35H located in the outer cylinder 42 were provided.

The connective tissue testing device 41 taken out from the inside of the living body was used to observe the connective tissue formed in the outer cylinder through-holes 34H and the periphery thereof and the connective tissue formed in the inner cylinder through-holes 35H and the periphery thereof.

In the observation of the connective tissue, immersion of the connective tissue covering the inner surface of the outer cylinder 42 and the hole inner surfaces of the outer cylinder through-holes 34H in ethanol and immersion of the connective tissue in xylene were repeated, and paraffin embedment was performed to replace moisture by paraffin, thereby forming a paraffin-embedded block of the connective tissue. Subsequently, a section was cut out from the paraffin-embedded block, with the section including the outer cylinder through-hole 34H and the connective tissue on the periphery thereof. A Masson's trichrome staining of the section was performed, and the stained section was encapsulated on glass with an encapsulating medium.

Subsequently, the section sealed with the encapsulating medium was photographed at an observation magnification of 10 times, and a blue portion through an H filter in an HSV space was extracted as a collagen portion. The collagen portion is a neointima produced by intimal formation. The collagen portion indicates completion of intimal formation, and is a layer with collagen randomly oriented from the surface of the connective tissue rather than a layer with fibrous collagen collectively oriented in a bundle form. The following evaluations 1 and 2 were performed on the basis of the observation of the extracted collagen portion. In evaluation 2, the term "embolized" means that the outer cylinder through-hole 34H is completely filled with the collagen portion, or that the size of a gap formed in the collagen portion at the outer cylinder through-hole 34H is 0.01 mm or less.

(Evaluation 1) Whether or not intimal formation by the connective tissue is completed throughout the outer cylinder 42.

(Evaluation 2) Whether or not the outer cylinder through-hole 34H is embolized by the connective tissue.

Similarly, in the observation of the connective tissue, immersion of the connective tissue covering the inner surface of the inner cylinder 43 and the hole inner surfaces of the inner cylinder through-holes 35H in ethanol and immersion of the connective tissue in xylene were repeated, and paraffin embedment was performed to replace moisture by paraffin, thereby forming a paraffin-embedded block of the connective tissue. Subsequently, a section was cut out from the paraffin-embedded block, with the section including the inner cylinder through-hole 35H and the connective tissue on the periphery thereof. A Masson's trichrome staining of the section was performed, and the stained section was encapsulated on glass with an encapsulating medium.

Subsequently, the section sealed with the encapsulating medium was photographed at an observation magnification of 10 times, and a blue portion through an H filter in an HSV space was extracted as a collagen portion formed into an intima. The following evaluations 3 and 4 were performed on the basis of the observation of the extracted collagen portion. In evaluation 4, the term "patent" means that a gap having a width of 0.1 mm or more is formed in the collagen portion at the inner cylinder through-hole 35H.

(Evaluation 3) Whether or not intimal formation by the connective tissue is completed throughout the inner cylinder 43.

(Evaluation 4) Whether or not the inner cylinder through-hole 35H after intimal formation is patent.

As (i) a test simulating an environment in which intimal formation proceeds relatively easily, connective tissue testing devices 41 were provided in which the opening size, the opening occupancy, and the surface density of boundary of the outer cylinder through-hole 34H were changed as described below.

As (ii) a test simulating an environment in which intimal formation relatively hardly proceeds, connective tissue testing devices 41 were provided in which the opening size, the opening occupancy, and the surface density of boundary of the inner cylinder through-hole 35H were changed as described below, and the outer cylinder through-hole 34H had an opening size of 0.3 mm and an opening occupancy of 60%.

Opening size: 0.01 mm or more and 0.3 mm or less
Distance between the centers of openings: 0.03 mm or more and 0.7 mm or less
Opening occupancy: 15% or more and 60% or less
Surface density of boundary: 2.5/mm or more and 120/mm or less
Embedment period: 1 month Some of the combinations of the opening size, the distance between the centers of openings, the opening occupancy, and the surface density of boundary of the through-holes 22 in the square grid and the rhombic grid used in the test examples are shown below as [Opening Size, Distance between Centers of Openings, Opening Occupancy, Surface Density of Boundary].

[0.3 mm, 0.84 mm, 20%, 2.7/mm]
[0.3 mm, 0.68 mm, 31%, 4.1/mm]
[0.3 mm, 0.59 mm, 41%, 5.4/mm]
[0.2 mm, 0.56 mm, 20%, 4.0/mm]
[0.2 mm, 0.50 mm, 25%, 5.0/mm]
[0.2 mm, 0.45 mm, 31%, 6.1/mm]
[0.2 mm, 0.42 mm, 36%, 7.1/mm]
[0.2 mm, 0.39 mm, 41%, 8.1/mm]
[0.2 mm, 0.35 mm, 50%, 10.0/mm]
[0.15 mm, 0.42 mm, 20%, 5.3/mm]
[0.15 mm, 0.38 mm, 25%, 6.7/mm]
[0.15 mm, 0.34 mm, 31%, 8.1/mm]
[0.15 mm, 0.32 mm, 36%, 9.5/mm]
[0.15 mm, 0.30 mm, 41%, 10.8/mm]
[0.15 mm, 0.27 mm, 50%, 13.4/mm]
[0.12 mm, 0.34 mm, 20%, 6.7/mm]
[0.12 mm, 0.30 mm, 25%, 8.4/mm]
[0.12 mm, 0.27 mm, 31%, 10.2/mm]
[0.12 mm, 0.25 mm, 36%, 11.9/mm]

[0.12 mm, 0.24 mm, 41%, 13.5/mm]
[0.12 mm, 0.21 mm, 50%, 16.7/mm]
[0.10 mm, 0.28 mm, 20%, 8.0/mm]
[0.10 mm, 0.25 mm, 25%, 10.0/mm]
[0.10 mm, 0.20 mm, 41%, 16.2/mm]
[0.10 mm, 0.18 mm, 50%, 20.0/mm]
[0.06 mm, 0.17 mm, 20%, 13.4/mm]
[0.06 mm, 0.15 mm, 25%, 16.7/mm]
[0.06 mm, 0.12 mm, 41%, 27.0/mm]
[0.06 mm, 0.11 mm, 50%, 33.4/mm]
[0.04 mm, 0.11 mm, 20%, 20.0/mm]
[0.04 mm, 0.10 mm, 25%, 25.1/mm]
[0.04 mm, 0.09 mm, 26%, 29.6/mm]
[0.04 mm, 0.09 mm, 31%, 30.5/mm]
[0.04 mm, 0.08 mm, 36%, 35.6/mm]
[0.02 mm, 0.06 mm, 20%, 40.1/mm]
[0.02 mm, 0.05 mm, 31%, 60.9/mm]
[0.02 mm, 0.05 mm, 25%, 50.2/mm]
[0.02 mm, 0.04 mm, 21%, 41.3/mm]
[0.02 mm, 0.04 mm, 41%, 80.9/mm]

The connective tissue testing device 41 was provided which includes two types of holes having different sizes, i.e. first through-holes 22A as large holes and second through-holes 22B as small holes which fill gaps between adjacent first through-holes 22A for each of the outer cylinder through-hole 34H and the inner cylinder through-hole 35H, as shown in FIG. 12. The opening size of the first through-hole 22A is a first opening size. The opening size of the second through-hole 22B is a second opening size. The distance between opening edges of first through-holes 22A is a distance between first edges. The distance between opening edges of second through-holes 22B is a distance between second edges. Some of the combinations of the first opening size, the second opening size, the distance between first edges, the distance between second edges, the opening occupancy, and the surface density of boundary are shown below as [First Opening Size, Second Opening Size, Distance between First Edges, Distance between Second Edges, Opening Occupancy, Surface Density of Boundary].

[0.2 mm, 0.02 mm, 0.2 mm, 0.08 mm, 28%, 11.0/mm]
[0.2 mm, 0.02 mm, 0.2 mm, 0.03 mm, 37%, 29.0/mm]
[0.3 mm, 0.02 mm, 0.3 mm, 0.08 mm, 28%, 9.3/mm]

Figure 13:
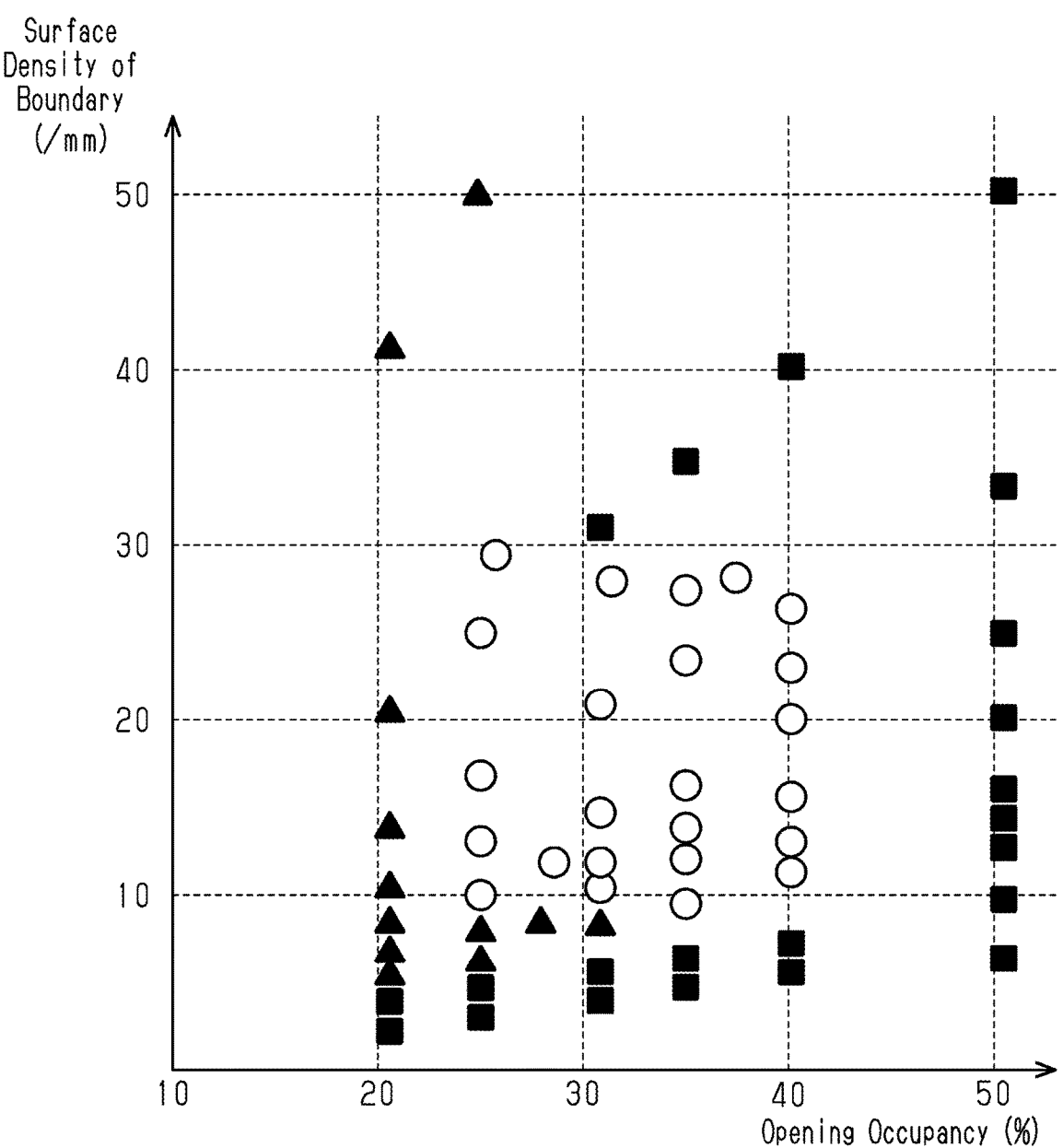
FIG. 13 is a graph showing the relationship between the state of a connective tissue and an opening occupancy and a surface density of boundary.

The white circle in FIG. 13 indicates a level at which it is recognized that intimal formation has been completed throughout the outer cylinder 42 (good in evaluation 1), that the outer cylinder through-hole 34H has been embolized (good in evaluation 2), that intimal formation has been completed throughout the inner cylinder 43 (good in evaluation 3), and that the inner cylinder through-hole 35H is patent (good in evaluation 4).

The black square mark in FIG. 13 indicates a level at which it is recognized that intimal formation has been uncompleted in a part of the inner peripheral surface of the outer cylinder 42 (poor in evaluation 1) or that the outer cylinder through-hole 34H has not been embolized (poor in evaluation 2).

The black triangle mark in FIG. 13 indicates a level at which it is recognized that intimal formation has been uncompleted in a part of the inner peripheral surface of the inner cylinder 43 (poor in evaluation 3) or that the inner cylinder through-hole 35H is not patent (poor in evaluation 4).

As shown in FIG. 13, a device having an opening size of 0.2 mm or more and 0.3 mm or less, an opening occupancy of less than 25%, and a surface density of boundary of less than 5/mm was rated poor in evaluation 1 or evaluation 2 as in the patency of the outer cylinder through-hole 34H. That is, a device with a level at which conditions 1, 2 and 3 were not satisfied was rated poor in evaluation 1 or evaluation 2.

A device having an opening size of 0.01 mm or more and less than 0.2 mm, an opening occupancy of less than 25%, and a surface density of boundary of 5/mm or more was rated poor in evaluation 3 or evaluation 4 as in the embolization of the inner cylinder through-hole 35H. That is, a device with a level at which conditions 1 and 3 were satisfied and condition 2 was not satisfied was rated poor in evaluation 3 or evaluation 4.

A device having an opening size of 0.01 mm or more and 0.3 mm or less, an opening occupancy of 42% or more and 50% or less, and a surface density of boundary of 7/mm or more was rated poor in evaluation 1 or evaluation 2 as in the patency of the outer cylinder through-hole 34H. That is, a device with a level at which conditions 1 and 3 were satisfied and condition 2 was not satisfied was rated poor in evaluation 1 or evaluation 2.

A device having an opening size of less than 0.02 mm, an opening occupancy of 20% or more and 50% or less, and a surface density of boundary of 42/mm or more was rated poor in evaluation 3 or evaluation 4 as in the embolization of the inner cylinder through-hole 35H. That is, a device with a level at which condition 2 was satisfied and conditions 1 and 3 were not satisfied was rated poor in evaluation 3 or evaluation 4.

On the other hand, a device having an opening size of 0.02 mm or more and 0.2 mm or less, an opening occupancy of 25% or more and 41% or less, and a surface density of boundary of 9.5/mm or more and 30/mm or less was rated good in evaluations 1, 2, 3, and 4. That is, when conditions 1, 2 and 3 are satisfied, a situation in which it is difficult to obtain the closing property at the aneurysm opening portion (i) of the aneurysm 34 due to an increase in opening size and opening occupancy is prevented by specifying the surface density of boundary. A situation in which it is difficult to obtain the blood flow conservation property at the branch opening (ii) of the branch blood vessel 35 due to a decrease in surface density of boundary is prevented by specifying the opening occupancy.

Test Example B

An internal carotid aneurysm developed in an internal carotid artery (ICA) with a diameter of 4.2 mm and having a maximum length of 35 mm and an aneurysm opening portion length (neck) of 9.6 mm was set as an object to be treated, and an intravascular indwelling stent satisfying the above-described conditions 1, 2, and 3 was applied to treatment of the object to be treated. Angiography for examining blood flow was performed immediately before, immediately after, and 6 months after indwelling of the intravascular indwelling stent.

Here, a polyurethane film having a thickness of 0.02 mm was used as the polymer film 21. As the through-hole 22, a hexagonal hole having an opening size of 0.1 mm was used. The opening occupancy was set to 30%, and the surface density of boundary was set to 16/mm.

Among cerebral aneurysms, the object to be treated has a particularly large size and a particularly long aneurysm opening portion, and is a so-called refractory unruptured aneurysm. Further, one branch blood vessel was located at a site opposed to the aneurysm opening portion in the internal carotid artery (ICA) in the object to be treated. Such an object to be treated is difficult to completely cure by any of the conventional treatments such as surgical treatment in which the artery is held with a clip and intravascular treatment in which the aneurysm is embolized by a coil.

On the other hand, when the intravascular indwelling stent satisfying the above-described conditions 1, 2, and 3 was used, the blood flow in the aneurysm which had been observed in the angiographic image immediately before indwelling was found to be stagnant in the angiographic image immediately after indwelling. The blood flow in the branch blood vessel which had been observed in the angiographic image immediately before indwelling was also observed in the angiographic image immediately after indwelling. Blood clotting in the aneurysm and blood flow in the branch blood vessel were observed in the angiographic image six months after the indwelling.

Thus, according to the above-described embodiment, the following effects can be obtained.

(1) When the intravascular indwelling stent satisfies conditions 1, 2, and 3, (i) the through-hole 22 is embolized after intimal formation in an environment where cells contained in the biological tissue material easily move to the surface of the artificial material, and meanwhile, (ii) the intimal formation proceeds to the extent that blood flow is maintained even in an environment where cells contained in the biological tissue material are hardly attached to the surface of the artificial material. As a result, the blood flow conservation property of the branch blood vessel and the aneurysm opening portion embolization property are improved because the opening size is 0.04 mm or more and 0.15 mm or less, the opening occupancy is 25% or more and 41% or less, and the surface density of boundary is 9.5/mm or more and 30/mm or less.

(2) When the through-holes 22 include through-holes 22 having different opening sizes, it is possible to set a small opening size at a site required to have strength sufficient to support a blood vessel wall and set a large opening size at a site required to have flexibility. Setting the opening occupancy and the surface density of boundary within respective specific ranges in the intravascular indwelling stent considerably restricts structural freedom in the intravascular indwelling stent, and therefore availability of various opening sizes is particularly suitable from the viewpoint of increasing the degree of freedom of design.

(3) When the thickness of the polymer film is 1 μm or more, breakage of the polymer film 21 in the process of forming the polymer film 21 is prevented, so that labor required for forming the polymer film 21 is reduced.

(4) When the thickness of the polymer film is 100 μm or less, an increase in the depth of the through-hole 22, i.e. distance over which cells contained in the biological tissue material move, is prevented, so that the connective tissue required for intimal formation from the intravascular indwelling stent is easily formed inside the intravascular indwelling stent.

(5) When the through-holes 22 are located so as to fill gaps between adjacent circular wires, the intravascular indwelling stent ensures that the opening edges of the through-holes 22 as intimal formation initiation points are substantially uniformly arranged over the entire stent main body. As a result, it is possible to reduce a difference in progress of intimal formation that may occur due to uneven distribution of the through-holes 22. In this way, the effect of (1) above is inhibited from varying depending on arrangement of the intravascular indwelling stent in the blood vessel.

(6) When the opening size of the through-hole 22 is 0.06 mm or more and 0.12 mm or less, the opening occupancy is 30% or more and 35% or less, and the surface density of boundary is 14/mm or more and 20/mm or less, the viability of the above-described effect of improving the blood flow conservation property of the branch blood vessel 35 and the aneurysm opening portion embolization property.

The above-described embodiment can also be carried out with the following change made thereto.

The through-holes 22 in the polymer film 21 may include a group of through-holes 22. For example, six through-holes 22 defining hexagonal openings are arranged at grid points forming a hexagonal grid, and these six through-holes 22 form a hole group. The polymer film 21 may include the through-holes 22 such that the hole group is arranged at each grid point on a square grid. The distance between one hole group including through-holes 22 and another hole group including through-holes 22 may be larger or smaller than the distance between the centers of openings in a single hole group.

REFERENCE SIGNS LIST 2L, 2W Opening Size
11 Strut
12 Link
13 Unit Structure
21 Polymer Film
22 Through-Hole
31 Intima
32 Connective Tissue
33 Blood Clot
34 Aneurysm
34E, 35E Opening Edge
35 Branch Blood Vessel
41 Connective Tissue Testing Device

The invention claimed is:

1. An intravascular indwelling stent that is indwelled in a blood vessel, comprising:
a stent main body being diametrically expandable and having a tubular shape; and
a polymer film covering the stent main body, wherein through-holes are formed in the polymer film, the through-holes connecting an inside and an outside of a cylinder of the intravascular indwelling stent to each other and each having an opening size from 0.02 mm to 0.2 mm, inclusive,
a ratio of an opening area of all the through-holes included in a unit area of an outer surface of the polymer film to the unit area is an opening occupancy,
a ratio of a length of opening edges of all the through-holes included in a unit area of the outer surface of the polymer film to the unit area is a surface density of boundary,
the opening occupancy is from 25% to 41%, inclusive, and
the surface density of boundary is from 9.5/mm to 30/mm, inclusive.

2. The intravascular indwelling stent according to claim 1, wherein the through-holes include through-holes having different opening sizes.

3. The intravascular indwelling stent according to claim 1, wherein the polymer film has a thickness from 1 μm to 100 μm, inclusive.

4. The intravascular indwelling stent according to claim 1, wherein
the stent main body is configured such that circular wires having repeated wavy bends along a circumferential direction of the intravascular indwelling stent are arranged in an extending direction of the intravascular indwelling stent, and the through-holes are located so as to fill gaps between the circular wires adjacent to each other.

5. The intravascular indwelling stent according to claim 1, wherein the opening size of the through-holes is from 0.06 mm to 0.12 mm, inclusive, the opening occupancy is from 30% to 35%, inclusive, and the surface density of boundary is from 14/mm to 20/mm, inclusive.

\* \* \* \* \*